United States Patent [19]

Mori

[11] Patent Number: 4,901,724
[45] Date of Patent: Feb. 20, 1990

[54] LIGHT RAY RADIATION DEVICE FOR USE IN MEDICAL TREATMENT

[76] Inventor: Kei Mori, 3-16-3-501,, Kaminoge, Setagaya-ku, Tokyo, Japan

[21] Appl. No.: 168,839

[22] Filed: Mar. 16, 1988

[30] Foreign Application Priority Data

Apr. 30, 1987 [JP]  Japan ................................ 62-108178

[51] Int. Cl.$^4$ .............................................. A61N 5/00
[52] U.S. Cl. ...................................... 128/372; 128/398
[58] Field of Search ............... 128/371, 372, 395, 396, 128/397, 398; 126/439, 351, 417

[56] References Cited

U.S. PATENT DOCUMENTS

| | | | |
|---|---|---|---|
| 668,404 | 2/1901 | Hanneborg | 128/372 |
| 1,677,393 | 7/1928 | Kideney | 128/374 |
| 2,493,328 | 1/1950 | Wandyak | 128/372 |
| 4,100,415 | 7/1978 | Blaisdell et al. | 128/371 |
| 4,582,062 | 4/1986 | Albini | 128/373 |
| 4,676,226 | 6/1987 | Mori | 126/439 |

FOREIGN PATENT DOCUMENTS

| | | | |
|---|---|---|---|
| 2740969 | 3/1979 | Fed. Rep. of Germany | 128/398 |
| 2183986 | 6/1987 | United Kingdom | 128/397 |

*Primary Examiner*—William H. Grieb
*Assistant Examiner*—Mark S. Graham
*Attorney, Agent, or Firm*—Jordan and Hamburg

[57] ABSTRACT

A light ray radiation device for use in medical treatment comprises an enclosed body having an inner surface capable of reflecting light rays and a cross-section made up of a polygon having an odd number of sides and an optical conductor for radiating visible light rays into the enclosed body. The device is constructed in such a way that the visible light rays can be reflected on the inner surface of the enclosed body and pass through the central portion of the enclosed body.

2 Claims, 4 Drawing Sheets

LIGHT RAY RADIATION DEVICE FOR USE IN MEDICAL TREATMENT

BACKGROUND OF THE INVENTION

The present invention refers to a light ray radiation device for use in medical treatment, in particular, to a light ray radiation device for use in medical treatment for promoting a living body reaction on the surface of the skin as well as under the skin by effectively radiating visible light rays onto the entire body's skin surface.

In recent years, man's life-span has increased and consequently larger numbers of persons suffer from incurable diseases such as arthritis, neuralgia and rheumatism, or from pain caused by injuries, bone fractures, or from illdefined diseases. Furthermore, persons cannot avoid growing old and having their skin age which progresses gradually from a comparatively young age. On the other hand, the present applicant has previously proposed to focus the sun's rays or artificial light rays by the use of lenses or the like, to guide the same into an optical conductor, and to transmit those same rays onto an optional desired place through the optical conductor. Those light rays transmitted in such a way are employed for use in illumination or for other like purposes as for example to cultivate plants, chlorella or the like. In the process thereof, visible light rays not containing therein ultraviolet rays, infrared rays, etc. promote a living body reaction.

In order to stop pain, it may be necessary to concentrate much radiated light onto the diseased part of a patient. However, even light rays of a weak intensity can have a beneficial effect on a disease if a sufficient length of time is allowed for radiating such light rays onto it. In practice, various medical treatments are administered by partially radiating weak light rays onto a diseased part. Furthermore, although it has been well known that sun-bathing is useful for promoting the health of a human body, the sun's rays contain therein ultraviolet rays or like harmful rays. Light rays such as ultraviolet rays exert a bad influence on the skin. In addition, a person who has not been healthy should not bathe in the sun. And furthermore, ultraviolet rays, and infrared rays have an accumulative effect. When ultraviolet rays are intense, cancer can develop. On the other hand, when infrared rays are intense, the radiated part becomes heated and is apt to get burned. It therefore isn't good for anyone's health to bathe for a long time in light rays containing therein ultraviolet and infrared rays.

In consideration of the above circumstances, the present applicant has previously proposed a light ray radiation device for use in medical treatment capable of radiating light rays which contain only visible light ray components and which contain no harmful components such as ultraviolet and infrared rays.

The present applicant has previously proposed a light ray radiation device or a light ray bathtub for use in medical treatment. The inner surface of the bathtub is mechanically processed into the form of a mirror. The bathtub has optical conductors in it's inner wall for supplying the visible light rays into the bathtub. The visible light rays radiated from the optical conductor are reflected onto the inner surface of the bathtub and almost uniformly radiated into the bathtub itself.

Moreover, although radiators for radiating light rays into the bathtub may be installed in the bathtub at uniformly spaced intervals of the distance, it may be possible to supply light rays of a stronger intensity to a certain part, as for instance a shoulder or to otherwise, or it may be possible to direct the light rays, radiated from each light ray radiation point of a smaller number of light radiators, toward the inner surface of the bathtub and to diffuse such light rays therefrom. The light ray bathtub is employed such that a naked person enters therein and bathes in the light rays radiated as mentioned above. For this reason, the bathtub is constructed such that it can be opened and closed by the use of a well known optional desired means.

Furthermore, since a person takes off one's clothes after entering the interior thereof, an undressing basket is unitarily attached to the bathtub. A head portion covering member is made of a transparent body such that the person entering the bathtub can see the state of the exterior thereof. The afore-mentioned head portion covering member is constructed such that it can also be opened and closed for the purpose of getting in touch with persons outside of the bathtub or for putting clothes into the basket. In addition, it may be easily understood that a wireless apparatus can be installed in the light ray bathtub, and a push button switch connected with the exterior thereof can be mounted on a board in the bathtub. Other well known means can be employed, all for the purpose of getting in touch with persons outside thereof.

And further, if a transparent bottom board is put on the bottom portion of the light ray bathtub and the light rays are radiated from the lower side of the bottom board, the light rays can be supplied to the sole of a foot which normally does not receive the light rays, for maintaining health by improving a person's blood circulation.

An apparatus for focusing the sun's rays or artificial light rays is attached to the end portion of an optical conductor cable and the light rays focused by the apparatus are guided into the optical conductor cable and transmitted therethrough. The light rays to be transmitted through the optical conductor for consist only of visible light rays containing therein neither ultraviolet nor infrared rays.

The light-receiving sockets of the optical conductor are provided onto the bathtub, and when the light ray bathtub is employed, the sockets are connected with the light-emitting socket of the optical conductor cable. The light rays transmitted through the optical conductor cable are delivered to the optical conductor installed in the inner wall of the bathtub through the sockets, and then radiated into the light ray bathtub in the manner mentioned before. The radiated light rays are reflected on the inner wall surface of the bathtub and almost uniformly supplied to the entire surface of a person's skin.

The temperature in the interior of the light ray bathtub is controlled. For instance, heated air or cooled air of a desired temperature is supplied into the bathtub through an air hose in order to control the temperature therein. When the bathtub is employed, the end portion of the air hose is connected with an air hose connecting mouth provided on the upper part of the light ray bathtub and temperature-controlled air is supplied from the upper part of the bathtub and discharged from the lower part thereof.

The light ray bathtub in which a person bathes while standing therein has been described heretofore. It may be also possible to bathe while sitting on a chair or lying down on a bed. In such cases, the shape of the bathtub needs to be changed depending on the posture of the person therein. For instance, its height is lowered a little or the type of bathtub is changed to a horizontal one from a vertical one. Such modifications are options as the occasion demands. However, in such cases, if the chair or the bed, to be put in the bathtub, is constructed of a transparent substance, it may be possible for the whole body of a person to bathe in the light rays.

SUMMARY OF THE INVENTION

It is an object of the present invention to provide a light ray radiation device for use in medical treatment for promoting a living body reaction on the surface of the skin as well as under the skin by effectively radiating visible light rays onto the entire body's skin surface.

It is another object of the present invention to provide a cylindrical body for use in medical treatment in which the light rays radiated into are effectively concentrated approximately in the central portion thereof.

It is another object of the present invention to provide an enclosed body in which the light rays are caused to pass through the almost central portion of it by the use of a simple and low-cost construction, and consequently the light rays can be more effectively radiated onto the diseased part of a patient by inserting the diseased part to be cured into the central portion of the enclosed body.

BRIEF DESCRIPTION OF THE DRAWINGS

FIGS. 4 and 5 are construction views for explaining an embodiment of a light ray radiation device for use in medical treatment according to the present invention, wherein FIG. 4 is a plane view thereof and FIG. 5 is a front view thereof.

DESCRIPTION OF THE PREFERRED EMBODIMENTS

Figure 1:
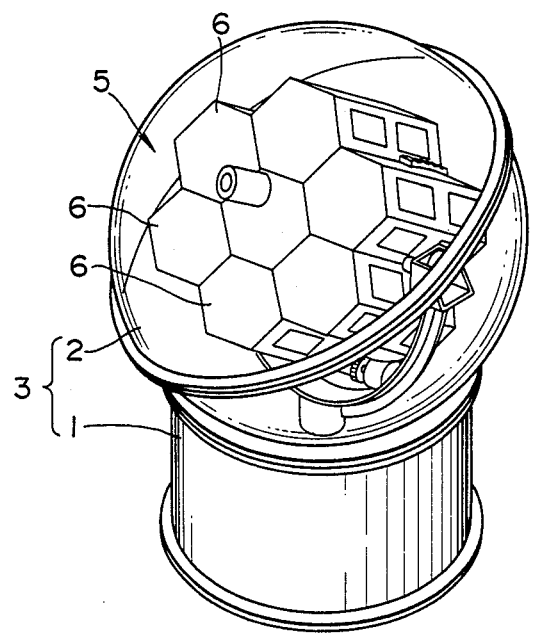
FIG. 1 is a perspective view showing an embodiment of the sun's ray collecting device previously proposed by the present applicant.

FIG. 1 is a perspective view showing an embodiment of the sun's ray collecting device previously proposed by the present applicant. In FIG. 1, 1 is a cylindrical foundation, 2 a dome-shaped head portion made of a transparent body, and 3 a capsule for use in the sun's ray collecting device constructed with the foundation 1 and the head portion 2. When the device is employed, the sun's ray collecting device 5 is accommodated in the capsule 3 as shown in FIG. 1. As is well known, the sun's ray collecting device comprises, for instance, a large number of lenses 6. The sun's rays focused by the lenses are guided into the optical conductor cables. The sun's rays guided in such a way are transmitted through the optical conductor cable onto an optical desired place.

Figure 2:
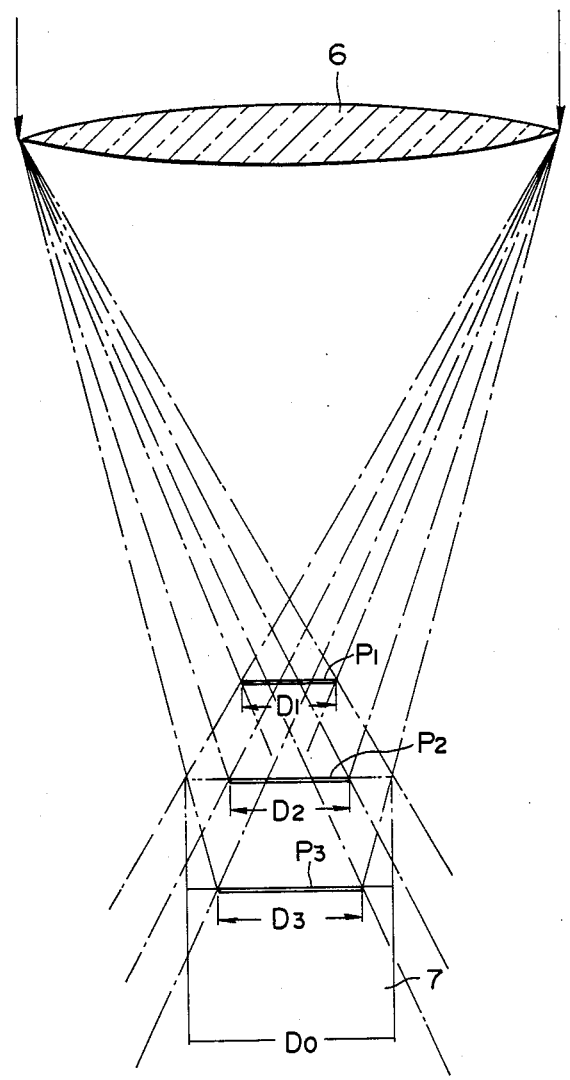
FIG. 2 is a detailed view for explaining an embodiment of the device which guides the visible light ray components of the sun's rays into the optical conductor cable.

FIG. 2 is a detailed view for explaining an embodiment of the device which guides the afore-mentioned light rays, corresponding to the visible light ray components of the sun's rays, into the optical conductor cable.

In FIG. 2, 6 is a lens consisting of a Fresnel lens or the like, and 7 is an optical conductor cable as mentioned before for guiding thereinto the sun's rays focused by the lens 6 and for transmitting the guided sun's rays therethrough. In the case of focusing the sun's rays by use of a lens system, the solar image has a central portion consisting of almost white-colored light rays and a circumferential portion containing therein a large amount of light ray components consisting of the wave lengths corresponding to the focal position of the lens system.

Namely, in the case of focusing the sun's rays, the position of the lens system and the size of the solar image will vary in accordance with the wave length of the light rays. For instance, the light rays of the color blue, having a short wave length, make a solar image of diameter $D_1$ at position $P_1$. Furthermore, the light rays of the color green make a solar image of diameter $D_2$ at position $P_2$, and the light rays of the color red make a solar image of diameter $D_3$ at position $P_3$.

Consequently, as shown in FIG. 2, when the light-receiving end-surface of the optical conductor cable 7 is put at position $P_1$, it is possible to collect the sun's rays containing plenty of light rays of the blue color component at the circumferential portion thereof. When the same is put at position $P_2$, it is possible to collect the sun's rays containing plenty of light rays of the green color component at the circumferential portion thereof. When the same is put at position $P_3$, it is possible to collect the sun's rays containing plenty of light rays of the red color component at the circumferential portion thereof. In each case, the diameter of the optical conductor cable is determined by the light ray components to be collected. For instance, the diameters thereof are $D_1$, $D_2$ and $D_3$, respectively, depending on the colors of the light rays to be stressed; i.e. the blue, green and red colors. In such a way, the consumed amount of the optical conductor cable can be reduced, and thereby the sun's rays containing therein plenty of light ray components of the desired color can be collected most effectively. And further, as shown in FIG. 2, if the diameter of the light-receiving end-surface of the optical conductor cable 7 is enlarged to $D_0$, it may be possible to collect visible light rays containing therein all of the wave length components.

Figure 3:
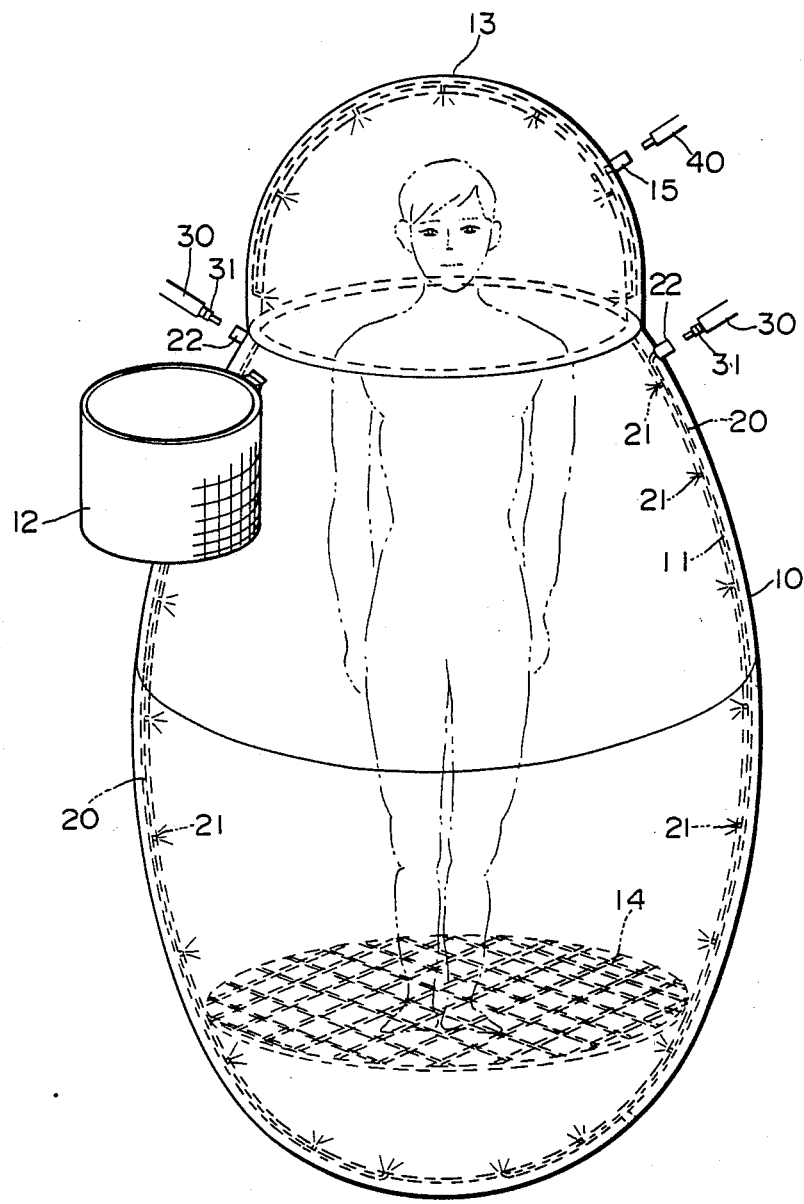
FIG. 3 is a perspective construction view for explaining an embodiment of the light ray radiation device for use in medical treatment as previously proposed by the present applicant.

The visible light rays transmitted through the optical conductor cable 7 in such a way as mentioned above are guided into a bathtub and discharged as shown in FIG. 3.

FIG. 3 is a perspective view for explaining an embodiment of the light ray radiation device for use in medical treatment as previously proposed by the present applicant. In FIG. 3, the reference numeral 10 represents a light ray bathtub. The inner surface 11 of the bathtub 10 is mechanically processed into the form of a mirror. The reference numeral 20 represents an optical conductor for supplying the visible light rays into the light ray bathtub 10. The visible light rays radiated from the optical conductor 20 are reflected onto the inner surface of the bathtub 10 and almost uniformly radiated into the bathtub itself 10.

Moreover, although radiators for radiating light rays into the bathtub 10 may be installed in the bathtub 10 at uniformly spaced intervals of the distance as shown in FIG. 3, it may be possible to supply light rays of a stronger intensity to a certain part, as for instance a shoulder or to otherwise, direct the light rays, radiated from each light ray radiation point of a smaller number of light radiators, toward the inner surface of the bathtub 10 and to diffuse such light rays therefrom. As shown in FIG. 3, the light ray bathtub 10 is employed such that a naked person enters therein and bathes in the light rays radiated as mentioned above. For this reason, the bathtub 10 is constructed such that it can be opened and closed by the use of a well known optional desired means.

Furthermore, since a person takes off one's clothes after entering the interior thereof, an undressing basket 12 is unitarily attached to the bathtub 10. A head portion covering the member 13 is made of a transparent body such that the person entering the bathtub 10 can see the state of the exterior thereof. The afore-mentioned head portion covering member 13 is constructed such that it can also be opened and closed for the purpose of getting in touch with persons outside of the bathtub 10 or for putting clothes into the basket 12. In addition, it may be easily understood that a wireless apparatus can be installed in the light ray bathtub 10, and a push button switch connected with the exterior thereof can be mounted on a board in the bathtub 10. Other well known means can be employed, all for the purpose of getting in touch with persons outside thereof.

And further, if a transparent bottom board 14 is put on the bottom portion of the light ray bathtub 10 and the light rays are radiated from the lower side of the bottom board 14, the light rays can be supplied to the sole of a foot which normally does not receive the light rays, for maintaining health by improving a person's blood circulation.

The reference numeral 30 represents an optional conductor cable. An apparatus for focusing the sun's rays or artifical light rays (light rays generated by a xenon lamp) is attached to the end portion of the optical conductor cable 30 not shown in FIG. 3. The light rays focused by the apparatus are guided into the optical conductor cable 30 and transmitted therethrough. The light rays to be transmitted consist only of visible light rays containing therein neither ultraviolet nor infrared rays. Although the technology for guiding into the optional conductor only visible light rays not containing therein harmful rays had already been proposed by the present applicant, the explanation of such technology is omitted because it has no immediate connection with the present invention.

The light-receiving side socket of the optical conductor 20 is represented by the reference numeral 22. When the light ray bathtub 10 is employed, the socket 22 is connected with the light-emitting side socket 31 of the optical conductor cable 30. The light rays transmitted through the optical conductor cable 30, as mentioned before, are delivered to the optical conductor 20 through the medium of both sockets 22 and 31, which are connected with each other, and then radiated into the light ray bathtub 10 in the manner mentioned before. The radiated light rays are reflected on the inner wall surface 11 of the bathtub 10 and almost uniformly supplied to the entire surface of a person's skin.

The temperature in the interior of the light ray bathtub 10 is controlled. For instance, heated air or cooled air of a desired temperature is supplied into the bathtub 10 through an air hose 40 in order to control the temperature therein. When the bathtub 10 is employed, the end portion of the air hose 40 is connected with an air hose connecting mouth 15 provided on the upper part of the light ray bathtub 10 and temperature-controlled air is supplied from the upper part of the bathtub 10 and discharged from the lower part thereof.

The light ray bathtub in which a person bathes while standing therein has been described heretofore. It may be also possible to bathe while sitting on a chair or lying down on a bed. In such cases, the shape of the bathtub 10 needs to be changed depending on the posture of the person therein. For instance, its height is lowered a little or the type of bathtub is changed to a horizontal one from a vertical one. Such modifications are options as the occasion demands. However, in such cases, if the chair or the bed, to be put in the bathtub 10, is constructed of a transparent substance, it may be possible for the whole body of a person to bathe in the light rays.

Figure 4:
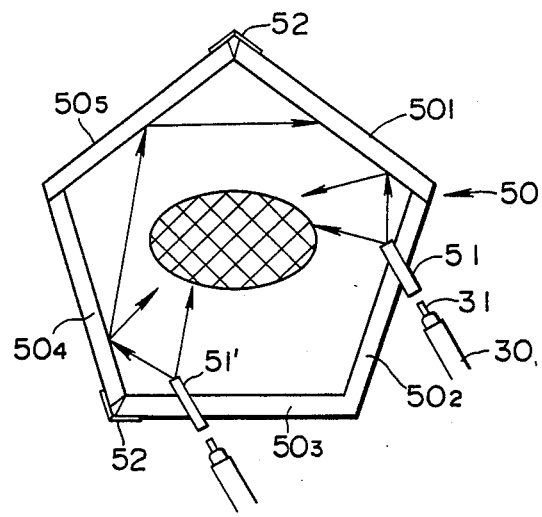
Figure 5:
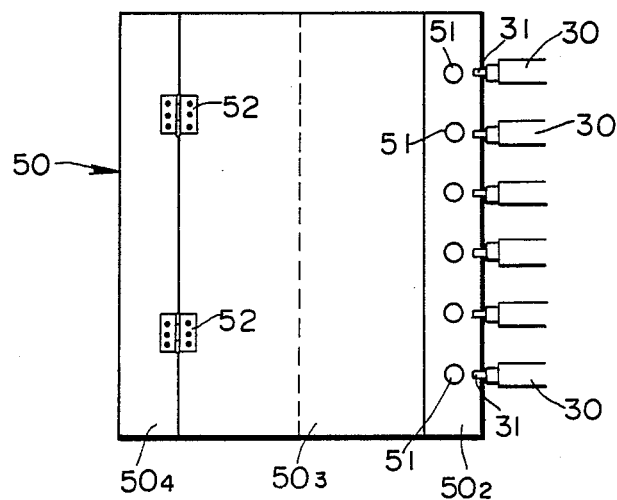

FIGS. 4 and 5 are views for explaining an embodiment of a light ray radiation device for use in medical treatment according to the present invention. FIG. 4 is a plane view thereof and FIG. 5 is a front view thereof. In FIGS. 4 and 5, the reference numerals $50_1$ to $50_5$ represent flat plates(reflecting plates) respectively having the inner surface formed in the form of a reflecting mirror. Those flat plates are integrally unified into one and make up an enclosed body having a pentagonal cross-section as shown in FIG. 4. The reference numeral 51 represents a connecting mouth for connecting an optical conductor cable, which is mounted on the enclosed body 50. The socket 31 of the optical conductor cable 30 is connected with the connecting mouth 51, and the light rays transmitted through the optical conductor cable 30 are radiated into the enclosed body 50.

The light rays radiated into the enclosed body 50 are reflected onto the reflecting plates $50_1$ to $50_5$ so as to go around inside the enclosed body 50. Finally, the majority of the light rays are concentrated to pass through the almost central portion thereof. Consequently, when an object 60 to be radiated such as a patient's arm is inserted into the central portion of the enclosed body 50, the light rays are almost uniformly radiated onto the circumference of the patient's arm. Moreover, the object to be radiated isn't limited to the arm. Any other part such as a leg, the body, the neck, the head or the like can be treated by the light rays. Preferably, the enclosed body 50 is pre-cast so that its size can fit those parts of the human body. At the time of treatment, since the putting in or taking out of the part of the body such as the neck is very difficult when using the cylindrical body 50, if at least one reflecting plate, to state an example shown in FIG. 4, the reflecting plates $50_4$ and $50_5$ are constructed so that those plates can be freely opened and closed respectively by the use of a hinge 52 and the enclosed body 50 can be used very conveniently. Furthermore, in the case of putting the entire human body in the enclosed body 50, it can be used in the same way as the previously proposed arrangement of FIG. 3 as mentioned before. The enclosed body 50 can be used for the vertical (standing) type and for the horizontal (lying-down) type. For instance, in the case of using the vertical type, a bottom plate having an inner side formed as a reflective mirror surface is mounted on the bottom portion in the enclosed body 50, and further, a transparent stand or a transparent chair is put on the bottom plate. By the use of such a construction, the light rays can be radiated evenly onto the sole of the patient's foot. On the other hand, in the case of using the horizontal type, a bed or the like, constructed with a transparent member, may be put therein for a like purpose.

An example in which the direction of the light rays' radiation is established in a one-way rotational direction has been described heretofore. However, if the direction thereof is established in another rotational direction by means of another optical conductor cable connecting the mouth shown by the reference numeral 51', the light rays can be uniformly dispersed. Although the example of the enclosed body having a pentagonal cross-section has been described heretofore, other enclosed bodies respectively having various polygonal crosssections, for instance, the cross-section of a triangle, a seven-cornered polygon, and a (2n+1)-cornered polygon (the enclosed bodies having no parallel surfaces) can also exert the same effect as that of the afore-mentioned embodiment i.e. the enclosed body having a pentagonal cross-section.

As is apparent from the foregoing description, according to the present invention, it may be possible that the light rays are caused to pass through the almost central portion of the enclosed body by the use of a simple and low-cost construction, and consequently the light rays can be more effectively radiated onto the diseased part of a patient by inserting the diseased part to be cured into the central portion of the enclosed body.

I claim:

1. A light ray radiation device according to claim 2, wherein said first and said second directions are rotational directions with said longitudinal axis of said enclosure means being the center thereof.

2. A light ray radiation device for use in medical treatment of a person's body or a person's body part comprising a hollow enclosure means having a longitudinal axis and a plurality of elongated flat side plates generally parallel to said axis, said side plates being arranged as a polygon to thereby define a hollow interior of said enclosure means, said polygon having an odd number of side plates, said side plates having interior surfaces which reflect light rays, first optical conductor means for conducting the visible light ray component of solar rays from which ultraviolet and infrared rays have been excluded, first connecting means mounted in and extending through one of said side plates, said first conductor means having an end portion which is mounted in said first connecting means such that said visible light ray component of solar rays conducted by said first conductor means is emitted from said first conductor means into the interior of said hollow enclosure means, said end portion of said first conductor means having a longitudinal axis which is disposed at an acute angle relative to said one side plate such that said emitted light ray component is reflected by said odd number of side plates so as to pass from one side plate to another side plate around the interior of said hollow enclosure means in a first direction to provide for radiation of a person or a person's body part disposed in said hollow enclosure means, second optical conductor means for conducting the visible light ray component of solar rays from which ultraviolet rays and infrared rays have been excluded, and second connecting means mounted in and extending through another of said side plates, said second conductor means having an end portion which is mounted in said second connecting means such that said visible light rays component of solar rays conducted by said second conductor means is emitted from said second conductor means into the interior of said hollow enclosure means, said end portion of said second conductor means having a longitudinal axis which is disposed at an acute angle relative to said another side plate such that said emitted light ray component is reflected by said odd number of side plates so as to pass from one side plate to another side plate around the interior of said hollow enclosure means in a second direction which is opposite to said first direction to thereby provide for substantially uniform radiation of said person's body or said person's body part.

* * * * *